United States Patent
Kellner et al.

[11] Patent Number: 6,098,627
[45] Date of Patent: Aug. 8, 2000

[54] BITE-BLOCK FOR PROTECTING THE MOUTH OF A PATIENT RECEIVING ELECTROCONVULSIVE THERAPY

[76] Inventors: Charles H. Kellner, 1744 Ion Ave., Sullivan's Island, S.C. 29482; Betsy K. Davis, 2011 Hwy. 17N #1800Q, Mount Pleasant, S.C. 29464; Carol Burns, 3902 Waterway Blvd., Isle of Palms, S.C. 29451

[21] Appl. No.: 09/128,845
[22] Filed: Aug. 4, 1998
[51] Int. Cl.[7] .................................................. A61C 5/14
[52] U.S. Cl. ........................ 128/859; 128/861; 128/862
[58] Field of Search .................................. 128/846, 848, 128/859–862

[56] References Cited

U.S. PATENT DOCUMENTS

| | | | |
|---|---|---|---|
| 2,694,397 | 11/1954 | Herms | 128/861 |
| 2,708,931 | 5/1955 | Freedland | 128/861 |
| 4,867,147 | 9/1989 | Davis | 128/859 |
| 5,235,991 | 8/1993 | Minneman | 128/861 |

*Primary Examiner*—Michael A. Brown
*Attorney, Agent, or Firm*—Robert Samuel Smith

[57] ABSTRACT

A bite-block for protecting the mouth of a patient receiving electroconvulsive therapy includes a U-shaped frame made from a unitary piece of a flexible material, such as expanded polyethylene foam, having a first side and an opposite second side. The U-shaped frame includes a body portion and two spaced-apart lobes extending therefrom. The two lobes define a gap therebetween. A force absorbing pad extends upwardly from the first side along at least a portion of each of the two lobes. A handle portion may be added so that the frame is Y-shaped.

6 Claims, 2 Drawing Sheets

BITE-BLOCK FOR PROTECTING THE MOUTH OF A PATIENT RECEIVING ELECTROCONVULSIVE THERAPY

BACKGROUND OF THE INVENTION

1. Field of the Invention

The present invention relates to medical devises and, more specifically, to an apparatus for protecting the mouth of a patient receiving electroconvulsive therapy.

2. Description of the Prior Art

Electroconvulsive therapy (ECT) remains a standard clinical treatment for severe depression. It involves a series of treatments given under general anesthesia in a specially equipped treatment suite. An electrical current is either passed across the patient's forehead (bilateral ECT) or across two points over the right hemisphere (unilateral ECT) in order to induce a brief generalized seizure. During the passage of the electrical stimulus, despite the fact that the patient has been given a systemic muscle relaxant (succinylcholine), the masseter muscles contract forcefully, necessitating the use of a bit-block or mouth guard to protect the tongue, teeth, and other oral tissues.

For many years, it has been the standard of care to use a hard rubber bite-block. Such rubber bite blocks function adequately, but they are firm and do not have optimal energy-absorbing characteristics. A significant number of patients using rubber bite blocks complain of jaw pain and soreness after ECT. Some of this may be attributable to the fact that the firm rubber bite-block is too firm. In addition, the standard rubber bite-block requires cleansing after each use in the same patient and then autoclaving to make it sterile for use in a different patient.

Recently, a part-foam, part-cardboard disposable bite-block has become available. Although an improvement over prior devices, it does not absorb optimal amounts of force. The foam and cardboard bit block has the disadvantage of being stiff and, therefore, difficult to place in the patient'mouth. Furthermore, it requires several steps to manufacture, thereby increasing unit cost.

SUMMARY OF THE INVENTION

The disadvantages of the prior art are overcome by the present invention which, in one aspect, is a bite-block for protecting the mouth of a patient receiving electroconvulsive therapy. The bit block includes a U-shaped frame made from a flexible material and having a first side and an opposite second side. The U-shaped frame includes a body portion and two spaced-apart lobes extending therefrom. The two lobes define a gap therebetween. Two force absorbing pads each extend upwardly from the first side along at least a portion of a different one of the two lobes.

In another aspect, a handle portion extends upwardly from the body portion of the frame, making the frame Y-shaped.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
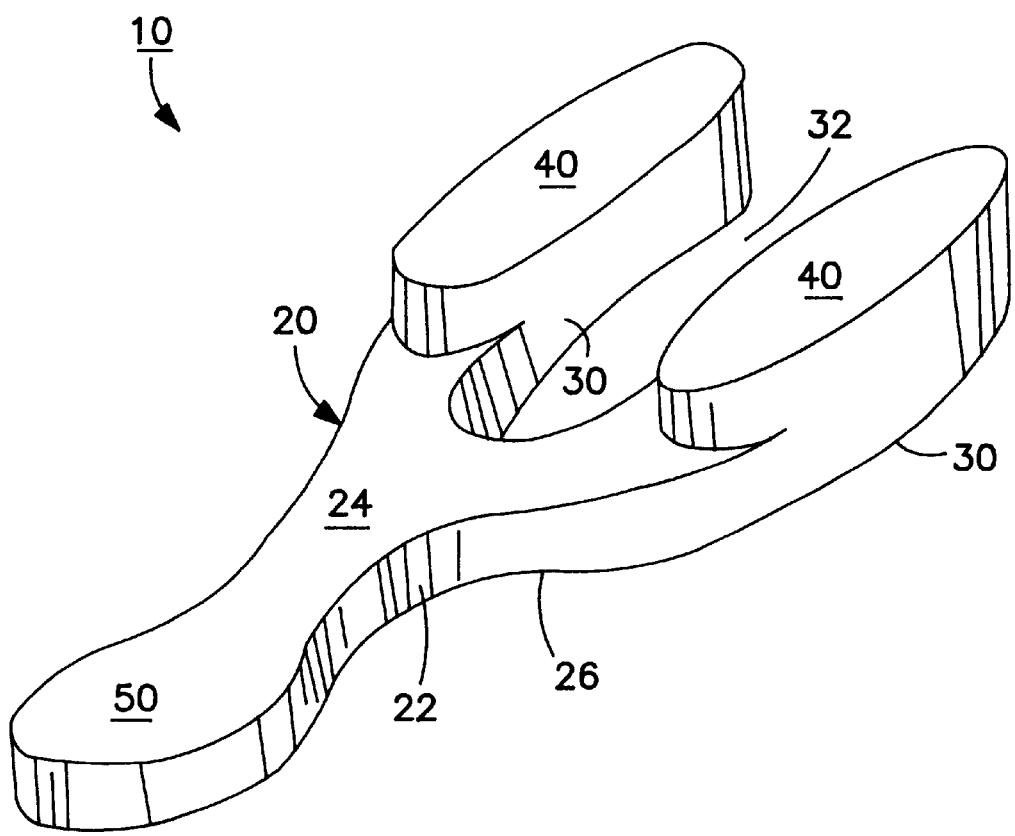
FIG. 1 is a top front perspective view of one embodiment of the invention.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Figure 2A:
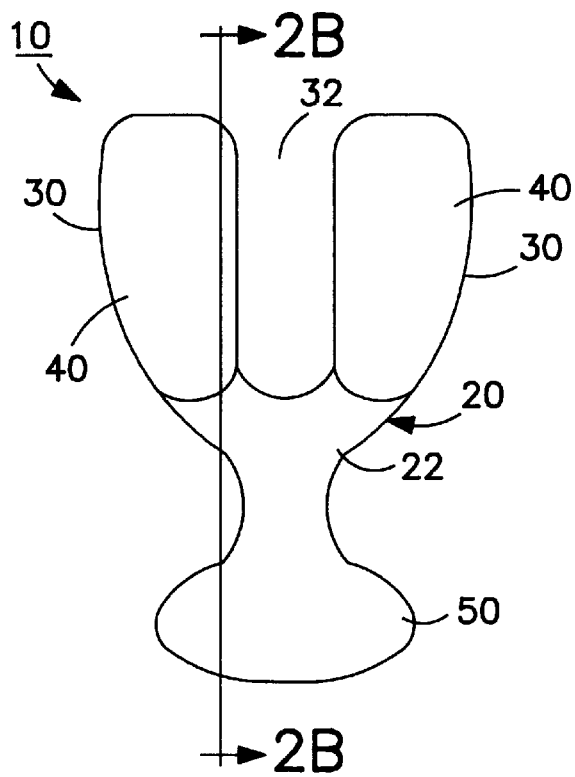
FIG. 2A is a top plan view of the embodiment of FIG. 1.
Figure 2B:
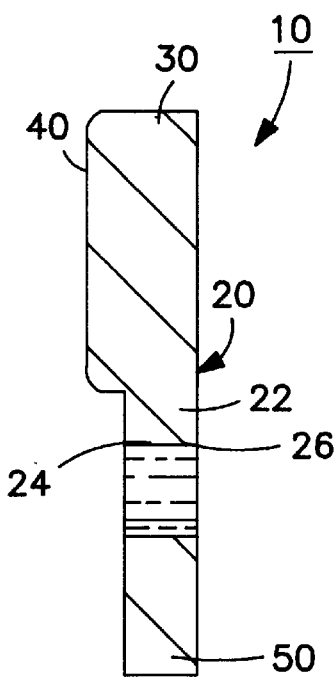
FIG. 2B is a cross-sectional plan view of the embodiment of FIG. 2A, taken along lines 2B—2B.

As shown in FIGS. 1, 2A and 2B, one embodiment of the invention is a bite-block 10 for protecting the mouth of a patient receiving electroconvulsive therapy. The bite-block 10 includes a flexible Y-shaped frame 20 having a first side 24 and an opposite second side 26. The Y-shaped frame 20 has a body portion 22 and two spaced-apart lobes 30 extending therefrom. The two lobes 30 define a gap 32 therebetween. A handle portion 50 extends upwardly from the body portion 22 opposite the two lobes 30. The handle portion 50 may be of any suitable shape in order to provide a means for readily gripping the bite-block 10 so that it may be easily placed and properly positioned within the patient's mouth and removed therefrom after treatment. Two force absorbing pads 40 each extend upwardly from the first side 24 along at least a portion of a different one of the two lobes 30.

The force absorbing pads 40 and the lobes 30 must be thick enough to absorb the force exerted on them during a session of ECT. In one embodiment, they are 2.0 cm thick. However, different thicknesses could be used, depending upon such variables as the size of the patient's mouth and the strength of the patient's masseter muscles.

The width of the gap 32 must be sufficient so that when the lobes 30 are fully squeezed together, the bite block 10 is easily placed in the patient's mouth. The gap 32 should also form an airway. The gap 32 also provides a guide for the patient's tongue, thereby preventing the patient's tongue from getting lodged between the patient's teeth. In one embodiment, the width of the gap 32 is 1.5 cm. It will be understood that the dimensions of the gap 32, the Y-shaped from 20 and the pads 40 would depend on several factors, such as the size and age of the patient, the intensity and duration of the treatment session, and the expected force placed on the pads 40.

Each lobe 30, pad 40 and the Y-shaped frame 20 are made from a unitary piece of expanded polyethylene. The expanded polyethylene has a density in a range of from 3 pounds per cubic foot to 6 pounds per cubic foot. Having this density, the Y-shaped frame is flexible enough so that the two lobes 30 may be squeezed together to facilitate easy placement of the bite-block 10 in the patient's mouth, while also providing the force-absorbing ability necessary to prevent damage to the patient's tissues when the masseter muscles contract forcefully during a session of ECT treatment.

Because the bite-block 10 is made of a unitary piece of foam, it can be made inexpensively enough so that it is disposable after a single use. This further reduces the cost of the ECT treatment because disposability eliminates the added cost associated with sterilization.

Figure 3:
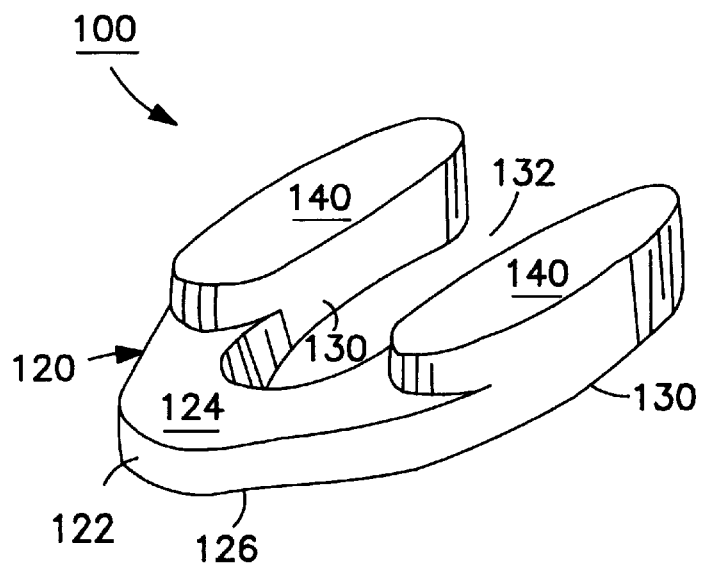
FIG. 3 is a top front perspective view of a second embodiment of the invention.

As shown in FIG. 3, another embodiment of the bite-block 110, in accordance with the invention, does not include a handle portion 50. This embodiment includes a flexible U-shaped frame 120 having a first side 124 and an opposite second side 126. The U-shaped frame 120 a body portion 122 and two spaced-art lobes 130 extending therefrom. The two lobes 130 define a gap 132 therebetween. Two force absorbing pads 140 each extend upwardly from the first side 124 along at least a portion of each one of the two lobes 130. This embodiment, lacking a handle, may be somewhat harder to place in and remove from the patient's mouth than the embodiment of FIG. 1, but, obviously, has relatively lower material costs.

The embodiments disclosed above may be manufactured by making an aluminum mold of the bite-block. Polyethylene beads are transferred into the cavity of the mold and then steam is introduced into the cavity. The steam softens the beads and the beads fuse. The mold and the beads are then allowed to cool. As is obvious to those of skill in the art, other manufacturing processes and materials may be employed without departing from the scope of the invention.

The above described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. A bite block for protecting the mouth of a patient receiving electroconvulsive therapy comprising:
    a U shaped frame of a flexible material having a first side and an opposite second side and including a body portion and two spaced apart lobes extending therefrom, the two lobes defining a gap therebetween; and
    two force absorbing pads, each extending upwardly from the first side along a at least a portion of a different one of the two lobes,
    said U-shaped frame and two absorbing pads formed from a unitary piece of foam wherein said foam is selected to have the U-shaped frame sufficiently flexible to provide that the two lobes may be squeezed together to facilitate easy placement of the bite-block (10) in the patient's mouth, while also providing the force absorbing ability necessary to protect the mouth of a patient receiving electroconvulsive therapy when the masseter muscles contract forcibly during a session of ECT treatment.

2. The bite-block of claim 1, wherein the unitary piece of foam comprises expanded polyethylene.

3. The bite-block of claim 2, wherein the expanded polyethylene has a density in a range of from 3 pounds per cubic foot to 6 pounds per cubic foot.

4. The bite-block of claim 1, further comprising a handle portion extending upwardly from the body portion of the U-shaped frame, opposite the two lobes.

5. A bite block for protecting the mouth of a patient receiving electroconvulsive therapy comprising:
    a Y shaped frame of a flexible material having a first side and an opposite second side and including a body portion and two spaced apart lobes extending therefrom, the two lobes defining a gap therebetween and handle portion extending upwardly from the body potion opposite the two lobes; and
    two force absorbing pads, each extending upwardly from the first side along at least a portion of a different one of the two lobes,
    each lobe pad and the Y-Shaped frame being made from a unitary piece of expanded foam wherein said foam has a flexibility selected to enable that the two lobes are squeezable together whereby placement of the bite-block (10) in the patient's mouth is facilitated while also providing the force absorbing ability necessary to protect the mouth of a patient receiving electroconvulsive therapy when the masseter muscles contract forcibly during a session of ECT treatment.

6. The bite-block of claim 5, wherein the expanded polyethylene has a density in a range of from 3 pounds per cubic foot to 6 pounds per cubic foot.

* * * * *